United States Patent [19]

Bruneau

[11] Patent Number: 5,036,083

[45] Date of Patent: Jul. 30, 1991

[54] HETEROCYCLIC AGENTS

[75] Inventor: Pierre A. R. Bruneau, Ludes, France

[73] Assignees: ICI Pharma, France; Imperial Chemical Industries PLC, England

[21] Appl. No.: 373,494

[22] Filed: Jun. 30, 1989

[30] Foreign Application Priority Data

Jul. 15, 1988 [EP] European Pat. Off. ............ 88401845

[51] Int. Cl.$^5$ ..................... A61K 31/44; C07D 473/00
[52] U.S. Cl. .................................... 514/338; 546/271
[58] Field of Search ....................... 546/271; 548/359; 514/338, 405

[56] References Cited

U.S. PATENT DOCUMENTS 4,045,564  8/1977  Berntsson ...................... 546/271 X

FOREIGN PATENT DOCUMENTS 0284174  9/1988  European Pat. Off. .

OTHER PUBLICATIONS

Chemical Abstracts Service 110: 192811 (abstract of European Patent 284,174).
Kametani et al., "Studies on the Syntheses of Azole Derivatives, Part II(1), Syntheses of N-(1- or 2-Substituted)indazolones via Diazotization (2),", *Journal of Heterocyclic Chemistry*, vol. 7, No. 4, Aug. 1970, pp. 815–820.
Wyrick et al., "Hypolipidemic Activity of Phthalimide Derivatives, 7, Structure–Activity Studies of Indazolone Analogues", Journal of Medicinal Chemistry, vol. 27, No. 6, Jun. 1984, pp. 768–772.
Chemical Abstracts, vol. 27, No. 21, 20th Nov. 1972, p. 451, abstract No. 140065q.
Chemical Abstracts 4–Indazolinecarboxamide, N–butyl–3–oxo– (7Cl) CAOLD (prior to 1967).

Chemical Abstracts AN CA76(24);147252m.

*Primary Examiner*—Catherine S. Kilby Scalzo
*Attorney, Agent, or Firm*—Cushman, Darby & Cushman

[57] ABSTRACT

The invention concerns a 1,2-dihydro-3H-indazol-3-one derivative of formula I

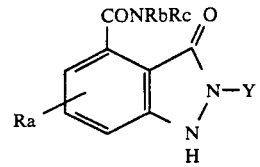

wherein
Ra is hydrogen, halogeno, hydroxy, cyano, trifluoromethyl, 1–6C)alkyl or (1–6C)alkoxy;
Rb is hydrogen or (1–6C)alkyl;
Rc is hydrogen, (1–8C)alkyl or (3–8C)alkenyl; and
Y is (1–8C)alkyl, (3–8C)alkenyl or (3–8C)alkynyl, or Y is a group of the formula —A—Q in which A is (1–6C)alkylene or (3–6C)alkenylene, and Q is phenyl, naphthyl, pyridyl, thienyl, isoxazolyl, thiazolyl or thiadiazolyl, which may optionally bear one or two substituents;
or a pharmaceutically-acceptable salt thereof;
or a (12–4C)alkoxycarbonyl derivative thereof.

The invention also concerns processes for the manufacture of an indazol-3-one of the formula I and pharmaceutical compositions containing said indazol-3-one. Also included in the invention is a method of treating various inflammatory or allergic diseases using an indazol-3-one of the formula I and the use of such a compound in the production of a new medicament for such use.

7 Claims, No Drawings

HETEROCYCLIC AGENTS

This invention concerns novel heterocyclic agents and more particularly novel indazolone derivatives which are inhibitors of the enzyme 5lipoxygenase (hereinafter referred to as 5-LO). The invention also concerns processes for the manufacture of said indazolone derivatives and novel pharmaceutical compositions containing said indazolone derivatives. Also included in the invention is the use of said indazolone derivatives in the treatment of various inflammatory and/or allergic diseases in which the direct or indirect products of 5-LO catalysed oxidation of arachidonic acid are involved, and the production of new medicaments for such use.

As stated above the indazolone derivatives described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as arthritic diseases, asthma, allergic rhinitis, atopic dermatitis, psoriasis, cardiovascular and cerebrovascular disorders and inflammatory bowel disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

In copending European Application No. 88300281.8 (published 28th Sept., 1988 as EP 0284174 A1) it is disclosed that certain indazolone derivatives are effective as inhibitors of the enzyme 5-LO and thus of leukotriene biosyntheses. It has subsequently been shown that certain compounds within the scope of that application possess redox properties, which properties may contribute to the inactivation of the enzyme 5-LO by reduction of an iron atom within the active site from the ferric (Fe (III)) to the ferrous (Fe (II)) oxidation level. However some redox inhibitors are known to induce methaemoglobin formation (F L Fort et alia, Fundamental and Applied Toxicology, 1984, 4, 216) and it has now been discovered that 1,2-dihydro-2-(3-pyridylmethyl) 3H indazol-3-one (Ex. 24 of EP 0284174 A1) when dosed orally to dogs at a dose of 5 mg/kg causes induction of methaemoglobin formation. There is therefore a need for an inhibitor of the enzyme 5-LO which does not possess this potentially serious side-effect.

We have now discovered that certain indazolone derivatives are effective as inhibitors of the enzyme 5-LO and thus of leukotriene biosyntheses. Moreover the indazolone derivatives of the invention do not cause the induction of significant levels of methaemoglobin at doses which produce significant inhibition of the enzyme 5-LO. Thus, such compounds are of value as therapeutic agents in the treatment of, for example, allergic conditions, asthma, cardiovascular and cerebrovascular disorders, and/or inflammatory and arthritic conditions, mediated alone or in part by one or more leukotrienes.

According to the invention there is provided a 1,2-dihydro-3H-indazol-3-one (hereinafter abbreviated to indazolone) derivative of the formula I (set out hereinafter) wherein Ra is hydrogen, halogeno, hydroxy, cyano, trifluoromethyl, (1–6C)alkyl or (1–6C)alkoxy;

Rb is hydrogen or (1–6C)alkyl;

Rc is hydrogen, (1–8C)alkyl or (3–8C)alkenyl: and

Y is (1–8C)alkyl, (3 8C)alkenyl or (3–8C)alkynyl, or

Y is a group of the formula A Q in which A is (1 6C)alkylene or (3–6C)alkenylene, and Q is phenyl, naphthyl, pyridyl, thienyl, isoxazolyl, thiazolyl or thiadiazolyl, which may optionally bear one or two substituents selected from halogeno, hydroxy, cyano, trifluoromethyl, amino, nitro, (1–6C)alkyl, (1–6C)alkoxy, (1–6C)alkylamino, di[(1–4C)alkyl]amino or (2–6C)alkanoylamino, or Q may bear a (1–4C)alkylenedioxy substituent;

or a pharmaceutically-acceptable salt thereof;

or a (1–4C)alkoxycarbonyl derivative thereof.

The chemical formulae referred to herein by Roman numerals are set out for convenience on a separate sheet hereinafter. In this specification the term "alkyl" includes both straight and branched alkyl groups but references to individual alkyl groups such as "propyl" are specific for the straight chain ("normal") version only, any branched chain isomer such as "isopropyl" being referred to specifically. An analogous convention applies to other generic terms.

It is to be understood that, insofar as certain of the compounds of formula I or their (1–4C)alkoxycarbonyl derivatives defined above may exist in optically active or racemic forms by virtue of one or more substituents containing an asymmetric carbon atom, the invention includes in its definition of active ingredient any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

Suitable values for Ra, or for Rb when it is (1–6C)alkyl, include the following, by way of example:

for halogeno: fluoro, chloro, bromo and iodo;

for (1–6C)alkyl: methyl, ethyl, propyl, isopropyl and butyl; and for (1–6C)alkoxy: methoxy, ethoxy, propoxy, isopropoxy and butoxy.

A suitable value for Rc or Y when it is (1–8C)alkyl is, for example, methyl, ethyl, propyl, isopropyl, butyl, isobutyl, sec-butyl, pentyl, isopentyl, hexyl, heptyl or octyl; when it is (3–8C)alkenyl is, for example, allyl, methylallyl, 2-butenyl, 3-butenyl, 3-methylbut-2-enyl or 2-hexenyl; or when it is (3–8C)alkyl is, for example, 2-propynyl, 2-butynyl, 3-butynyl or 2-hexynyl.

A suitable value for A when it is (1–6C)alkylene is, for example, methylene, ethylene, ethylidene, trimethylene, propylidene, tetramethylene or pentamethylene; or when it is (3–6C)alkenylene is, for example, 2-propenylene, 2-butenylene or 3-butenylene.

Suitable values for Q when it is naphthyl, pyridyl, thienyl, isoxazolyl, thiazolyl or thiadiazolyl include, for example, 1-naphthyl, 2-naphthyl, 2-pyridyl, 3-pyridyl, 4-pyridyl, 2-thienyl, 3-thienyl, 3-isoxazolyl, 4-isoxazolyl, 5-isoxazolyl, 2-thiazolyl, 4-thiazolyl, 5-thiazolyl, 1,2,5-thiadiazol-3-yl, 1,2,3-thiadiazol-4-yl or 1,2,3-thiadiazol-5-yl.

Suitable values for optional substituents which may be present on Q include, for example
   for halogeno: fluoro, chloro and bromo;
   for (1-6C)alkyl: methyl, ethyl, propyl and butyl;
   for (1-6C)alkoxy: methoxy, ethoxy, isopropoxy and butoxy;
   for (1-6C)alkylamino: methylamino, ethylamino, propylamino and butylamino;
   for di-[(1-4C)alkyl] amino: dimethylamino, diethylamino and dipropylamino;
   for (2-6C)alkanoylamino: acetamido, propionamido, butyramido and hexanamido; and
   for (1-4C)alkylenedioxy: methylenedioxy and ethylenedioxy.

A suitable value for a (1-4C)alkoxycarbonyl derivative of an indazolone of the formula I is, for example, a methoxycarbonyl, ethoxycarbonyl or t butoxycarbonyl derivative in which the alkoxycarbonyl group is located on Nl of the indazolone ring.

Suitable pharmaceutically acceptable salts include, for example, alkali metal (such as potassium or sodium), alkaline earth metal (such as calcium or magnesium), ammonium and aluminium salts, and salts with organic bases affording physiologically acceptable cations, such as salts with methylamine, dimethylamine, trimethylamine, piperidine and morpholine. In addition, for those indazolone derivatives which are sufficiently basic, suitable pharmaceutically-acceptable salts include physiologically-acceptable acid-addition salts such as salts with hydrogen halides, sulphuric acid and phosphoric acid.

A preferred compound of the invention comprises an indazolone of the formula I wherein
   Ra is hydrogen, fluoro, chloro, bromo, methyl, ethyl or methoxy;
   Rb is hydrogen, methyl or ethyl;
   Rc is hydrogen, methyl, ethyl, propyl, isopropyl, butyl, isobutyl,
   pentyI, hexyI, aIIyI oz methylaIIyl; and
   Y is methyl, ethyl. propyl, butyl, allyl or methylallyl, or Y is a group of the formula—A—Q wherein A is methylene, ethylene, ethylidene, trimethylene, ethylidene or 2-propenylene, and Q is phenyl, naphth 1-yl, 3-pyridyl, 4-pyridyl, 5-thiazolyl or 1,2,5-thiadiazol-3-yl, which may optionally bear fluoro, chloro, bromo, amino, methyl, ethyl or methoxy;
   or a pharmaceutically acceptable salt thereof;
   or a (1-4C)alkoxycarbonyl derivative thereof.

An especially preferred compound of the invention comprises
   an indazolone of the formula I wherein Ra is hydrogen; Rb is hydrogen:
   Rc is methyl, ethyl, propyl, butyl or pentyl; and
   Y is methyl or ethyl, or
   Y is a group of the formula—A—Q wherein A is methylene and Q is phenyl or 3-pyridyl;
   or a pharmaceutically-acceptable salt thereof:
   or a (1-4C)alkoxycarbonyl derivative thereof.

A specific especially preferred compound of the invention is, for example, a compound selected from the group consisting of 2-methyll-4-(N-methylcarbamoyl), 2-methyll-4-(N-ethylcarbamoyl), 2-methyll-4-(N-n-pentylcarbamoyl), 2-benzyl 4-(N-n-pentylcarbamoyl), 4-(N methylcarbamoyl) 2-(3-pyridylmethyl), 4-(N ethylcarbamoyl) 2-(3-pyridylmethyl) and 4-(N-n-pentylcarbamoyl) 2-(3-pyridylmethyl) 1,2-dihydro-3H-indazol 3-one; or a pharmaceutically-acceptable salt thereof; or a (1-4C)alkoxycarbonyl derivative thereof.

The compounds of the formula I may be obtained by conventional procedures of organic chemistry well known in the art for the manufacture of structurally analogous indazolones. Thus, for example, they may be obtained by the procedures analogous to those disclosed in "The Chemistry of Heterocyclic Compounds", (ed. R. H. Wiley, published by Interscience 1967), Vol. 22, Chapter 10, at pages 356-361, in "The Heterocyclic Compounds". (ed. R. C. Elderfield, published by Wiley 1957), Vol. 5, at pages 166-182, and in the article by L. Baiocchi and G. Palazzo (Synthesis, 1978, 633-648), the contents of which publications are incorporated herein by way of reference. The invention further includes the manufacture of an indazolone of the formula I, or of a (1-4C)alkoxycarbonyl derivative thereof, or of a pharmaceutically-acceptable salt thereof, by any one of such analogous procedures.

In particular, the invention includes the manufacture of an indazolone of the formula I as defined above by a process (a) which comprises deprotecting a protected indazolone derivative of the formula II wherein Ra, Rb, Rc and Y have the meanings defined hereinbefore and Rd is a protecting group.

Suitable examples of protecting groups Rd include, for example, acyl groups such as (1-4C)alkanoyl (especially acetyl), (1-4C)alkoxycarbonyl (especially methoxcarbonyl, ethox butoxycarbonyl) and aroyl (especially benzoyl). The deprotection conditions used for the above process necessarily vary with the nature of Rd. Thus, for example, acyl groups such as alkanoyl, alkoxycarbonyl and aroyl may be removed by, for example, hydrolysis with base such as an alkali metal hydroxide (for example lithium or sodium hydroxide) or acid such as hydrochloric, sulphuric or phosphoric acid, generally in the presence of an aqueous solvent or diluent such as a (1-4C)alkanol and at a temperature in the range, for example, 0° to 60° C. (conveniently at or about room temperature). It will be appreciated that, when a base is used for the deprotection, the indazolone is initially formed as the corresponding salt from which the free indazolone may be liberated by a conventional acidification process, for example by treatment with a mineral acid such as hydrochloric acid. The process is particularly adapted to the production of those compounds of formula I wherein Y is alkyl, alkenyl or a group—A—Q as previously defined. Alternatively acyl groups such as alkanoyl, alkoxycarbonyl and aroyl may be removed by, for example, treatment with base such as ammonia or a (1-4C)alkylamine (for example methylamine), generally in the presence of a diluent such as a (1-4C)alkanol and at a temperature in the range, for example, 0° to 80° C. (conveniently at or about room temperature).

The starting material of the formula II may be conveniently obtained, for example, by protecting an indazolone derivative of the formula III, for example by reacting it with a suitable acyl halide, or anhydride, such as a (1-4C)alkanoyl chloride or bromide, a (1-4C)alkanoic acid anhydride, benzoyl chloride, benzoic acid anhydride, or a (1-4C)alkoxycarbonyl chloride (which is preferred) under conventional acylation conditions, for example in the presence of a suitable base such as pyridine, 4-dimethylaminopyridine, triethylamine, morpholine or N methylmorpholine, to give a protected derivative of the formula IV wherein Rd has the meanings defined above. The latter derivative may then be reacted with an alkylating agent of the formula L-Y wherein L is a leaving group and Y has the meaning defined hereinabove. Suitable leaving groups, when Y is alkyl or alkenyl, or is a group of the formula—A—Q include, for example, halogeno (especially chloro, bromo or iodo) and alkane- or arenesulphonyloxy (especially methansulphonyloxy or p-toluenesulphonyloxy). The alkylation reaction is preferably performed in the presence of a suitable base, for example an alkali metal hydroxide, in a suitable inert solvent or diluent, for example t butyl methyl ether, tetrahydrofuran, 1,2-dimethoxyethane, N methylpyrrolidone or N,N-dimethylformamide. Alternatively, the protected indazolone derivative of the formula IV may be used in the form of its preformed anhydrous alkali metal salt, for example by prior reaction with a molecular equivalent of a suitable base such as sodium or potassium methoxide, ethoxide or hydride or butyl-lithium; in which case a wider range of conventional solvents such as (1–4C)alkanol diluents may be employed for the reaction with the alkylating agent of formula L Y. This procedure is particularly useful when Rd is a (1–4C)alkoxycarbonyl group. In either case, the alkylation is generally performed at a temperature in the range, for example, 10° to 100° C. and, conveniently, at or near ambient temperature.

It is to be understood that the reaction of a protected derivatives of the formula IV with an alkylating agent of the formula L-Y may, in addition, give rise to a compound isomeric with that of the formula II, i.e. in which Y is attached to the oxygen atom of the amide group. Such isomeric compounds may be separated by procedures well known to those skilled in the art, for example by column chromatography or by crystallisation.

The starting indazolone derivative of the formula III may be made by analogy with known indazolone synthetic procedures.

A further process (b) according to the invention for the manufacture of an indazolone of the formula I as defined hereinbefore comprises cyclising a 2-hydrazinobenzoic acid of the formula V, or a reactive derivative thereof, wherein Ra, Rb, R and Y have the meanings defined above.

The cyclisation may be carried out using a variety of conditions. For example, it may be carried out thermally by heating the free carboxylic acid at a temperature in the range, for example, 40°–120° C., under the influence of an acid catalyst such as acetic acid, propionic acid or a mineral acid (for example hydrochloric, sulphuric or phosphoric acid). Alternatively, the free carboxylic acid may be converted to a reactive derivative such as an acid halide, for example using phosphoryl chloride, oxalyl chloride or thionyl chloride at a temperature in the range, for example, 10° to 60° C., which halide may in certain cases spontaneously cyclise to the required indazolone of the formula I. An alternative reactive derivative of the carboxylic acid of the formula V is, for example, a (1–4C)alkyl, phenyl or benzyl ester of said acid, which derivatives may be cyclised, for example, by the influence of heat, optionally in the presence of an acidic or basic catalyst.

The starting 2-hydrazinobenzoic acid of the formula V may be obtained, by standard procedures of organic chemistry. Thus, for example, the compound of the formula V wherein Y is a group of the formula —CH$_2$.A$^1$—Q in which A$^1$ is a direct link to Q, (1–5C)alkylene or (2–5C)alkenylene and Q has the meaning defined hereinbefore or Y is a group of the formula —CH$_2$.Y$^1$ in which Y$^1$ is hydrogen, (1–7C)alkyl, (2–7C)alkenyl or (2–7C)alkynyl, may be obtained by reduction of a hydrazone of the formula VIa or VIb, for example using an alkali metal amalgam, borohydride or cyanoborohydride (especially sodium cyanoborohydride) in a suitable solvent or diluent such as a (1–4C)alkanol (for example ethanol or methanol) or an ether (for ex tetrahydrofuran or t butyl methyl ether) at a temperature in the range, for example, 10° to 50° C. The hydrazone of the formula VIa or VIb may itself be obtained by a conventional procedure involving reaction of an aldehyde of the formula H.CO.A$^1$.Q or H.CO.Y$^1$ with a hydrazine of the formula VII. The hydrazine of the formula VII may itself be obtained, for example, by a conventional reduction of a diazonium salt derived from the corresponding 2-aminobenzoic acid, for example using sodium sulphite, sulphur dioxide or stannous chloride as a reducing agent. The necessary 2-aminobenzoic acids and the aldehydes of the formula H.CO.A$^1$Q or H.CO.Y$^1$ are in general known or may be obtained by standard procedures of organic chemisty.

As will readily be appreciated process (b) is particularly suitable for the production of those compounds of the formula I wherein Y is a group of the formula —CH$_2$Q or CH$_2$Y$^1$ as defined above.

A further process (c) according to the invention for the manufacture of an indazolone of the formula I comprises cyclising a 2-aminobenzamide derivative of the formula VIII wherein Z is a suitab leaving group, for examnle hydroxy, acetoxy, methoxy or p-toluenesulphonyloxy.

The cyclisation may be carried out using a variety of conditions. For example, it may be carried out under conventional acid or base catalysis (which latter is generally preferred) at a temperature in the range, for example 40° to 120° C., in a suitable solvent or diluent, for example a (1–4C)alkanol (such as methanol or ethanol). A suitable base is, for example, an alkali metal hydroxide or (1–4C)alkoxide, such as sodium hydroxide, potassium hydroxide, sodium methoxide or potassium ethoxide.

The starting material of the formula VIII can be made by standard techniques of organic chemistry. Thus, for example, the compound of the formula VIII wherein Z is hydroxy may be obtained by reduction of the corresponding nitro compound of the formula IX using conditions known to produce the required hydroxylamine, for example using zinc or iron dust in the presence of a base such as an alkali metal hydroxide or ammonium acetate, at a temperature in the range, for example, 10° to 50° C. and in a suitable aqueous solvent of diluent such as methanol or ethanol.

The production of an indazolone of the formula I may therefore also be carried out by the preferred procedure of reacting a nitro compound of the formula IX with a suitable reducing metal, such as zinc or iron dust, in the presence of a strong base, such as an alkali metal hydroxide, in a suitable solvent or diluent such as a (1–4C)alkanol (e.g. methanol or ethanol, of which the latter is preferred), and at a temperature in the range, for example, 40° to 120° C.

The starting material of the formula IX may be obtained from the corresponding carboxylic acid of the formula X and the amine of the formula H$_2$N.Y using conventional amidification procedures which are standard techniques of organic chemistry.

A further process (d) according to the invention for the manufacture of an indazolone of the formula I which contains one or more phenolic hydroxy groups comprises deprotecting a suitably protected version of such a compound of the formula I.

Suitable phenolic hydroxy protecting groups include, for example, (1–6C)alkyl, (3–6C)alk-2-enyl, tri(1–4C)alkylsilyl, tetrahydropyran-2-yl, 1-aryl-(1–4C)alkyl, (1–6C)alkanoyl and aroyl (such as methyl, ethyl, t butyl, allyl, trimethylsilyl, tetrahydropyran-2-yl, benzyl, 1-phenylethyl, formyl, acetyl and benzoyl).

The deprotection reaction conditions necessarily depend on the protecting group used. However, in general, conditions which are standard in the art for the removal of the same protecting group in chemically analogous compounds are used. Thus, for example, when the protecting group is (1–6C)alkyl (and especially methyl) the deprotection may be carried out, for example, by use of boron tribromide at −80° C. to 20° C., optionally in a suitable solvent such as methylene chloride, or by heating with sodium thioethoxide in a suitable solvent, such as N,N-dimethylformamide or 1,3-dimethyl-3,4,5,6-tetrahydro-2-(1H) -pyrimidinone, at a temperature of, for example, 50° to 160° C. Alternatively, an ethyl or methyl protecting group may be removed, for example, by reaction with lithium diphenylphosphide in a suitable solvent or diluent, such as tetrahydrofuran or t butyl methyl ether, at a temperature in the range, for example, 0° to 60° C. Similarly, an alkanoyl or benzoyl protecting group may be removed, for example, by base catalysed hydrolysis (such as sodium or potassium hydroxide in an aqueous (1–4C)alkanol or glycol) at a temperature, for example, in the range 10° to 60° C. Similarly, an allyl or tetrahydropyran-2-yl protecting group may be removed, for example, by a conventional treatment with a strong acid such as trifluoroacetic acid. Similarly, a trimethylsilyl protecting group may be removed, for example, by conventional treatment with aqueous tetrabutylammonium fluoride or sodium fluoride, and a benzyl or 1-phenylethyl protecting group, for example, by treatment with sodium in liquid ammonia.

The necessary protected derivatives are obtainable by analogous procedures to those described hereinbefore or by modifications thereto within the ordinary skill of an organic chemist.

A further process (e) according to the invention for the production of an indazolone of the formulae I or II which contains one or two alkanoylamino groups comprises acylating a compound of the formula I or a compound of the formula II which contains one or two amino groups.

A particular suitable acylating agent is, for example, any agent known in the art for the acylation of amino to acylamino, for example an acyl halide, for example a (2–6C)alkanoyl chloride or bromide, in the presence of a suitable base, an alkanoic acid anhydride, for example a (2–6C)alkanoic acid anhydride, or an alkanoic acid mixed anhydride, for example the mixed anhydride formed by the reaction of an alkanoic acid and a (1–4C)alkoxycarbonyl halide, for example a (1–4C)alkoxycarbonyl chloride, in the presence of a suitable base. In general the reaction is carried out in a suitable solvent or diluent such as methylene chloride, acetone, tetrahydrofuran or t-butyl methyl ether and at a temperture, for example, at or near ambient temperature, that is in the range 15° to 35° C. A suitable base when it is required is, for example, pyridine, 4-dimethylaminopyridine, triethylamine, ethyldiisopropylamine, N-methylmorpholine, an alkali metal carbonate, for example potassium carbonate, or an alkali metal carboxylate, for example sodium acetate. It will be appreciated that when a compound of the formula I which contains one or two amino groups is subjected to reaction with an acylating agent there may be, in addition to acylation of the amino group, acylation of the unprotected nitrogen atom in the indazolone ring. It is well known to one skilled in the art how to separate such mixtures of compounds, for example by column chromatography or by crystallisation. It will also be appreciated that when a compound of the formula II is acylated a novel compound of the formula I can be produced by deprotecting the protected indazolone using conditions described under process (a) above.

A further process (f) according to the invention for the production of an indazolone of the formula I wherein Y is a group of the formula A—Q and there are one or two amino substituents in Q, comprises the reduction of the corresponding compound wherein there are one or two nitro substituents in Q. In general conditions which are standard in the art for the reduction of a nitro group are used. Thus, for example, the reduction may be carried out by the hydrogenation of a solution of the nitro compound in an inert solvent or diluent in the presence of a suitable metal catalyst, for example finely divided platinum metal (obtained by the reduction of platinum oxide in situ). A suitable inert solvent or diluent is, for example, an alcohol, for example methanol, ethanol or isopropanol, or an ether, for example tetrahydrofuran or t-butyl methyl ether. The reaction is generally carried out at a temperature at or near ambient temperature, that is in the range 15° to 35° C.

A further process (g) according to the invention for the production of an indazolone of the formula I wherein Y is a group of the formula—A—Q and wherein A is alkenylene comprises the reduction of the corresponding compound wherein A is alkynylene. In general conditions which are standard in the art for the reduction of an alkynylene group are used. Thus, for example, the reduction may be carried out by the hydrogenation of a solution of the alkynylene compound in an inert solvent or diluent in the presence of a suitable metal catalyst. A suitable inert solvent is, for example, an alcohol, for example methanol or ethanol, or an ether, for example tetrahydrofuran or t-butyl methyl ether. A suitable metal catalyst is, for example, palladium or platinum on an inert support, for example charcoal or barium sulphate. Preferably a palladium-on-barium sulphate catalyst is used to substantially prevent over-reduction of the alkynylene group to an alkylene group. The reaction is generally carried out at a temperature at or near ambient temperature, that is in the range 15° to 35° C.

When a pharmaceutically-acceptable salt of an indazolone of the formula I is required, it may be obtained, for example, by reaction of said compound with a suitable acid or base using a conventional procedure. When an optically active form an indazolone of the formula I is required it may be obtained by carrying out one of the aforesaid procedures using an optically active starting material, or by resolution of a racemic form of said compound using a conventional procedure.

As stated previously, the indazolones of the formula I are inhibitors of the enzyme 5-LO. The effects of this inhibition may be demonstrated, for example, using one or more of the standard procedures set out below:

(a) An in vitro spectrophotometric enzyme assay system, which assesses the inhibitory properties of a test compound in a cell free system using 5-LO isolated from guinea pig neutrophils and as described by D. Aharony and R. L. Stein (J. Biol. Chem., 1986, 261(25), 11512-11519). This test provides a measure of the intrinsic inhibitory properties against soluble 5-LO in an extracellular environment.

(b) An in vitro assay system involving incubating a test compound with heparinised rat blood, prior to challenge with the calcium ionophore A23187 and then indirectly measuring the inhibitory effects on 5-LO by assaying the amount of $LTB_4$ using the specific radioimmunoassay described by Carey and Forder (F. Carey and R. A. Forder, Brit. J. Pharmacol. 1985, 84, 34P) which involves the use of a protein-$LTB_4$ conjugate produced using the procedure of Young et alia Prostaglandins, 1983, 26(4), 605-613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for prostaglandin $E_2$ ($PGE_2$) described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

(c) An ex vivo assay system, which is a variation of test b) above, involving administration of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $PGE_2$. This test provides an indication of the bioavailability of a test compound as an inhibitor of 5-LO or cyclooxygenase.

(d) An in vitro assay system involving the measurement of the inhibitory properties of a test compound against the liberation of $LTC_4$ and $PGE_2$ induced by zymosan on mouse resident peritoneal macrophages, using the procedure of Humes (J. L. Humes et alia, *Biochem. Pharmacol* 1983, 32, 2319-2322) and conventional radioimmunoassay systems to measure $LTC_4$ and $PGE_2$. This test provides an indication of inhibitory effects against 5-LO and cyclooxygenase in a nonproteinaceous system.

(e) An in vivo system involving the measurement of the effects of a test compound in inhibiting the inflammatory response to arachidonic acid in the rabbit skin model developed by D. Aked et alia (*Brit. J. Pharmacol.*, 1986, 89, 431-438). This test provides an in for 5-LO inhibitors administered topically or orally.

(f) An in vivo system involving measuring the effects of a test compound administered orally or intravenously on a leukotriene dependent bronchoconstriction induced by an antigen challenge in guinea pigs pre-dosed with an antihistamine (mepyramine), a $\beta$-adrenergic blocking agent (propranolol) and a cyclooxygenase inhibitor (indomethacin), using the procedure of W. H. Anderson et alia (British *J Pharmacology*, 1983, 78(1), 67-574). This test provides a further in vivo test for detecting 5-LO inhibitors.

Although the pharmacological properties of the indazolones of the formula I necessarily vary with structural changes, in general compounds of the formula I possess 5-LO inhibitory effects at the following concentrations or doses in one or more of the above tests (a)-(f):

Test (a): $IC_{50}$ in the range, for example, 0.1-30$\mu$M;
Test (b): $IC_{50}$ ($LTB_4$) in the range, for example, 0.1-10$\mu$M $IC_{50}$ ($PGE_2$) in the range, for example, 15-200$\mu$M;
Test (c): oral ED50 ($LTB_4$) in the range, for example, 1-200 mg/kg;
Test (d): $IC_{50}$ ($LTC_4$) in the range, for example, 0.001-1$\mu$M, $IC_{50}$ ($PGE_2$) in the range, for example, 20-1000$\mu$M;
Test (e): inhibition of inflammation in the range, for example, 0.3-100$\mu$g intradermally:
Test (f): $ED_{50}$ in the range, for example, 0.5-10mg/kg i.v.

No overt toxicity or other untoward effects are present in tests (c), (e) and or (f) when compounds of the formula I are administered at several multiples of their minimum inhibitory dose or concentration. In addition, using conventional tests for the measurment of methaemoglobin formation, it was shown that no significant induction of methaemoglobin formation is caused when compounds of the formula I are administered at several multiples of the minimum inhibitory dose or concentration for the inhibition of the enzyme 5-LO.

Thus, by way of example, the compound 1,2-dihydro-2-methyll-4-(N-n-pentylcarbamoyl)-3Hindazol-3-one has an $IC_{50}$ of 3.1$\mu$M in test (a), and $IC_{50}$ pf 1.4$\mu$M against $LTB_4$ and of 72$\mu$M against $PGE_2$ in test (b), and an oral ED50 of 30-100 mg/kg versus in test (c). In general those compounds of the formula I which are particularly preferred have an $IC_{50}$ of $<\mu$M against $LTB_4$ and of $>50\mu$M against $PGE_2$ in test (b), and an oral $ED_{50}$ of $<100$ mg/kg against $LTB_4$ in test (c).

These compounds are examples of indazolones of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises an indazolone of the formula I, or a pharmaceutically-acceptable salt thereof, or a (1-4C)alkoxycarbonyl derivative thereof, as defined hereinbefore, in association with a pharmaceutically-acceptable diluent or carrier.

The composition may be in a form suitable for oral use, for example a tablet, capsule, aqueous or oily solution, suspension or emulsion; for nasal use, for example a snuff, nasal spray or nasal drops; for vaginal or rectal use, for example a suppository; for administration by inhalation, for example as a finely divided powder or a liquid aerosol: for sub-lingual or buccal use, for example a tablet or capsule; or for parenteral use (including intravenous, subcutaneous, intramuscular, intravascular or infusion), for example a sterile aqueous or oily solution or suspension.

In general the above compositions may be prepared in a conventional manner using conventional excipients.

The amount of active ingredient (that is an indazolone of the formula I, or a pharmaceutically-acceptable salt thereof, or a (1-4C)alkoxycarbonyl derivative thereo(f) that is combined with one or more excipients to produce a single dosage form will necessarily vary depending upon the host treated and the particular route of administration. For example, a formulation intended for oral administration to humans will generally contain, for example, from 0.5 mg to 2g of active ingredient compounded with an appropriate and convenient amount of excipients which may vary from about 5 to about 8 percent by weight of the total composition. Dosage unit forms will generally contain about 1 mg to about 500 mg of an active ingredient.

The invention also includes an active ingredient as defined above for use in medicine. By for use in medicine both prophylactic and therapeutic use of said active ingredient are encompassed.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of am active ingredient as defined above will naturally vary according to the nature and severity of the conditions, the age and sex of the animal or patient and the route of administration, according to well known principles of medicine. As mentioned above, indazolones of the formula I are useful in treating those allergic and inflammatory conditions which are due alone or in part to the effects of the metabolites of arachidonic acid arising by the linear (5-LO catalyse(d) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovasular disorders of an inflammatory nature, arthritic and inflammatory joint disease, and inflammatory bowel diseases.

In using an active ingredient as defined above for therapeutic or prophylactic purposes it will generally be administered so that a daily dose in the range, for example, 0.5mg to 75mg per kg body weight is received, given if required in divided doses. In general lower doses will be administered when a parenteral route is employed. Thus, for example, for intravenous administration, a dose in the range, for example, 0.5mg to 30 mg per kg body weight will generally be used. Similarly, for administration by inhalation, a dose in the range, for example, 0.5 mg to 25 mg per kg body weight will be used.

Although indazolones of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, indazolones of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises an indazolone of the formula I, or a pharmaceutically-acceptable salt thereof, or a (1–4C)alkoxycarbonyl derivative thereof as defined hereinbefore, in conjunction or admixture with a cyclooxygenase inhibitory non-steroidal anti-inflammatory agent (such as mentioned abov(e), and a pharmaceutically-acceptable diluent or carrier.

The cytoprotective effects of an indazolone of the formula I may be demonstrated, for example, in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionat(e), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporations in vacuo and work-up procedures were carried out after removal of residual solids by filtration;

(ii) operations were carried out at room temperature, that is in the range 18°–20° and under an atmosphere of an inert gas such as argon;

(iii) column chromatography (by the flash procedur(e) and medium pressure liquid chromatography (MPLC) were performed on Herck Kieselgel silica (Art. 9385 obtained from E. Meck, Darmstadt, W. Germany;

(iv) yields are given for illustration only and are not necessarily the maximum attainable;

(v) the end products of the formula I have satisfactory microanalyses and their structures were confirmed by NMR and mass spectral techniques;

(vi) intermediates were not generally fully characterised and purity was assessed by thin layer chromatographic, infra-red (IR) or NMR analysis; and (vii) melting points are uncorrected and were determined using a Koffler block apparatus: melting points for the end-products of the formula I were determined after recrystallisation from a conventional organic solvent such as ethanol, methanol, acetone, ether or hexane, alone or in admixture.

EXAMPLE 1

1,2-Dihydro-1-carboethoxy- 4-(N-methylcarbamoyl)-3-H-indazol-3-one one (3.84 g) was added portionwise to a stirred suspension of sodium hydride [50% w/w dispersion in oil, 0.7 g, from which the oil was washed using petrol (b.p. 60°–80° C.)] in dimethylformamide (20 ml) and the mixture was stirred at ambient temperature for 30 minutes. Methyl iodide (1.1 ml) was added and the mixture was stirred at ambient temperature for 1 hour. Water (50 ml) and 0.1 N aqueous hydrochloric acid solution was added to bring the mixture to pH 6 and the mixture was extracted with ethyl acetate (3×50 ml). The combined organic extracts were washed with saturated aqueous sodium chloride solution, dried (MgSO4) and evaporated. The residue was triturated under a mixture of petrol (b.p. 60°-80° C.) and diethyl ether and the solid product was filtered off. There was thus obtained 1,2-dihydro-1-carboethoxy-2-methyll-4-(N-methylcarbamoyl)-3H-indazol-3-one (3.4 g, 78%) m.p. 132+-134° C.

A solution of the material so obtained (1.15 g) in methanol (20 ml) was stirred at ambient temperature and gaseous methylamine was bubbled into the solution for 5 minutes. The mixture was then stirred at ambient temperature for 30 minutes. The mixture was evaporated and the residue was purified by column chromatography eluting with a 19/1 v/v mixture of methylene chloride and methanol. There was thus obtained 1,2-dihydro-2-methyll-4-(N-methylcarbamoyl)-3H-indazol-3-one (0.73 g, 86%), m.p. 225°-250° C.

The 1,2-dihydro-1-carboethoxy-4-(N-methylcarbamoyl)-3H-indazol-3-one starting material was obtained as follows:

A solution of 3-acetoxy-1-acetyl-1H indazole-4-carbonyl chloride [prepared from the corresponding 4-carboxylic acid (10.5 g) using the procedure described in UK Patent Specification Number 339592 (Chemical Abstracts, 76, 147252 m)] in methylene chloride (20 ml) was added dropwise to a mixture of methylamine hydrochloride (3.9 g), triethylamine (12.5 ml) and methylene chloride (100 ml) which had been cooled to 0° C. The mixture was stirred at ambient temperature for 1 hour and evaporated. The residue was dissolved in methanol (100 ml), the solution was saturated with gaseous methylamine and the mixture was heated to reflux for 3 hours. The mixture was evaporated, the residue was dissolved in water (100 ml) and 1N aqueous hydrochloric acid solution was added to bring the mixture to pH 4. The precipitated solid was collected and dried. There was thus obtained 1,2-dihydro-4-(N-methylcarbamoyl)-3H-indazol-3-one (5.9 g, 82%), m.p. 178°-180° C.

Ethyl chloroformate (6.64 ml) was added dropwise to a mixture of the material so obtained (5.9 g) and pyridine (26 ml) which had been cooled to 0° C. The mixture was then heated to reflux for 45 minutes, cooled to ambient temperature and poured into water (100 ml). The precipitated solid was collected and dried. There was thus obtained 1,2-dihydro-1-carboethoxy-(N-methylcarbamoyl)-3H-indazol-3-one (7.6 g, 94%).

EXAMPLE 2

Using a similar procedure to that described in Example 1 but starting from 1,2-dihydro-1-carboethoxy-4-(N-ethylcarbamoyl)-3H-indazol-3-one there were obtained in turn 1,2-dihydro-1-carboxyethoxy-4-(N-ethylcarbamoyl)-2-methyl-3Hindazol-3-one as a solid, m.p. 129--20 121° C., in 82% yield, and 1,2-dihydro-4-(N-ethylcarbamoyl)-2-methyl--3H-indazol-3-one as a solid, m.p. 192°-194° C., in 73% yield.

The starting material was obtained from 3-acetoxy-1-acetyl-1H-indazole-4-carbonyl chloride using the procedure described in the corresponding portion of Example 1 except that ethylamine hydrochloride was used in place of methylamine hydrochloride. There were thus obtained in turn 1,2-dihydro-4-(N ethylcarbamoyl)-3H-indazol-3-one as an oil in 100% yield which was used without further Purification and 1,2-dihydro-1-carboethoxy-4-(N-ethylcarbamoyl) 3H-indazol-3-one as a solid, m.p. 209°-210° C., in 70% yield.

EXAMPLE 3

3 Picolyl chloride hydrochloride (2 g) was added portionwise to a mixture of 1,2-dihydro-1-carboethoxy-4-(N-methylcarbamoyl)-3H-indazol-3-one (3 g), cesium carbonate (8.2 g) and dimethylformamide (25 ml) and the mixture was heated to 50° C. for 1 hour. Acetic acid was added to bring the mixture to pH 7 and then the mixture was evaporated. There was thus obtained as a solid 1,2-dihydro-1-carboethoxy-4-(N-methylcarbamoyl-2-( 3-pyridylmethyl)-3H-indazol-3-one (1.8 g, 47%) which was used without further purification.

The product so obtained was treated with methylamine using the procedure described in the second paragraph of Example 1. There was thus obtained 1,2-dihydo-4-(N-methylcarbamoyl)-2-(3-pyridylmethyl)-3H-indazol-3-one as a solid, m.p. 182°-184° C., in 72% yield.

EXAMPLE 4

Using a similar procedure to that described in the first paragraph of Example 3 but starting from 1,2-dihydro-1-carboethoxy-4-(N-ethylcarbamoyl)-3H-indazol-3-one there was obtained 1,2-dihydro-1-carboethosy-4-(N-ethylcarbamoyl)-2-(3-pyridylmethyl(3H-indazol-3-one as an oil in 54% yield.

The product so obtained was treated with methylamine using the procedure described in the second paragraph of Example 1. There was thus obtained 1,2-dihydro-4-(N-ethylcarbamoyl)-2-3-pyridylmethyl)-3H-indazol-3-one as a solid, m.p. 197°-198° C., in 50% yield.

EXAMPLE 5

Using a similar procedure to that described in the first paragraph of Example 1 but starting from 1,2-dihydro-1-carboethoxy-4-(N-n-pentylcarbamoyl)-3Hindazol-3-one there was obtained 1,2-dihydro-1-carboethoxy-2-methyl-4-(N-n-pentylcarbamoyl)-3H-indazol-3-one as an oil in 100% yield.

A mixture of the product so obtained (4 g), 2N aqueous sodium hydroxide solution (12 ml) and methanol (40 ml) was heated to 50° C. for 15 minutes. The mixture was evaporated. Water (30 ml) was added, 1N aqueous hydrochloric acid solution was added to bring the mixture to pH 3 and the mixture was extracted with ethyl acetate (3×50 ml). The combined organic extracts were washed with a saturated aqueous sodium chloride solution, dried (MgSO4) and evaporated. The residue was purified by column chromatography eluting with a 19/1 v/v mixture of methylene chloride and methanol. There was thus obtained 1,2-dihydro-2-methyl-4-(N-n-pentylcarbamoyl)-3H -indazol-3-one (2.13 g, 68%), m.p. 128°-129° C. recrystallised from a mixture of water and ethanol).

The 1,2-dihydro-1-carboethoxy-4-(N-n-entylcarbamoyl)-3Hindazol-3-one starting material was obtained as follows:

A solution of 3-acetoxy-1-acetyl-1H-indazole-4-carbonyl chloride [prepared from the corresponding 4-carboxylic acid (1.8-g) using the procedure described in UK Patent Specification Number 133959] in methylene chloride (10 ml) was added dropwise to a mixture of n-pentylamine (0.88 ml) and triethylamine (12.5 ml).

The mixture was stirred at ambient temperature for 1 hour and evaporated. The residue was dissolved in ethyl acetate (25 ml), washed with 0.1N aqueous hydrochloric acid solution and evaporated. The residue was dissolved in methanol (5 ml) and 1N aqueous sodium hydroxide solution (3.5 ml) was added. The mixture was stirred at ambient temperature for 15 minutes, poured into water (10 ml), acidified with 1N aqueous hydrochloric acid solution and extracted with ethyl acetate (3×25 ml). The combined organic extracts were washed with water, dried (MgSO$_4$) and evaporated. The residue was purified by column chromatography eluting with a 19/1 v/v mixture of methylene chloride and methanol. There was thus obtained 1,2-dihydro-4-(N-N-pentylcarbamoyl)-3H-indazol-3-one (1.22 g, 77%), m.p. 167°–169° C.

The material so obtained was treated with ethyl chloroformate using the procedure described in the second paragraph of the portion of Example 1 which is concerned with the preparation of the starting material. There was thus obtained 1,2-dihydro-1-carboethoxy-4-(N-n-pentylcarbamoyl)-3H-indazol-3-one as a solid, m.p. 145°–146° C., in 78% yield.

These reactions were repeated to give the required quantity of starting material.

EXAMPLE 6

A mixture of 1,2-dihydro-1-carboethoxy-4-(N-n-pentylcarbamoyl)-3H-indazol-3-one (1g), benzyl bromide (0.74 ml), sodium iodide (45 mg), triethylamine (0.87 ml) and chloroform (40 ml) was heated to reflux for 10 hours. The mixture was evaporated and petrol (b.p. 60–80oC) was added to the residue. The mixture was filtered and the filtrate was evaporated to give a mixture of 1,2-dihydro-2-benzyl-1-carboetheoxy-4-(N-n-pentylcarbamoyl)-3H-indazol-3-one and 3-benzyloxy-1-carboethoxy-4-(N-n-pentylcarbamoyl)-1H-indazole as an oil (0.87 g, 68%) which was used without further purification.

The mixture so obtained was treated with an aqueous sodium hydroxide solution using the procedure described in the second paragraph of Example 5. There was thus obtained 1,2-dihydro-2-benzyl-4-(N-n-pentylcarbamoyl)-3H-indazol-3-one as a solid, m.p. 121°–121° C., in 67% yeild.

EXAMPLE 7

A solution of diisopropyl azodicarboxylate (4.96 g) in tetrahydrofuran (40 ml) was added dropwise to a mixture of 1,2-dihydro-1-carboethoxy-4-(N-n-pentylcarbamoyl)-3H-indazol-3-one (5.35 g), triphenylphosphine (6.6 g), 3-hydroxymethylpyridine (2 g) and tetrahydrofuran (60 ml). The mixture was stirred at ambient temperature for 40 minutes and evaporated. The residue was dissolved in ethyl acetate (100 ml) and extracted with 2N aqueous hydrochloric acid solution (2×50 ml). The combined aqueous extracts were neutralised by the addition of aqueous sodium bicarbonate solution and extracted with ethyl acetate (3×50 ml). The combined organic extracts were washed with water, dried (HgSO$_4$) and evaporated. There was thus obtained a mixture of 1,2-dihydro-1-carboethoxy-4-(N-n-pentylcarbamoyl)-2-(3-pyridylmethyl)-3H-indazol-3-one and 1-carboethoxy-4-(N-n-pentylcarbamoyl-3-(3-pyridylmethoxy)-1H-indzaole as an oil (6.8 g, 98%) which was used without further purification.

The mixture so obtained was treated with an aqueous sodium hydroxide solution using a similar procedure to that described in the second paragraph of Example 5 except that the reaction was carried out at ambient temperature for 1 hour and 1N aqueous hydrochloric acid solution was added to bring the mixture to pH 7. There was thus obtained 1,2-dihydro-4-(N-n-pentylcarbamoyl)-2-(3-pyridylmethyl)-3Hindazol-3-one as a solid, m.p. 112°–117° C., in 20% yield.

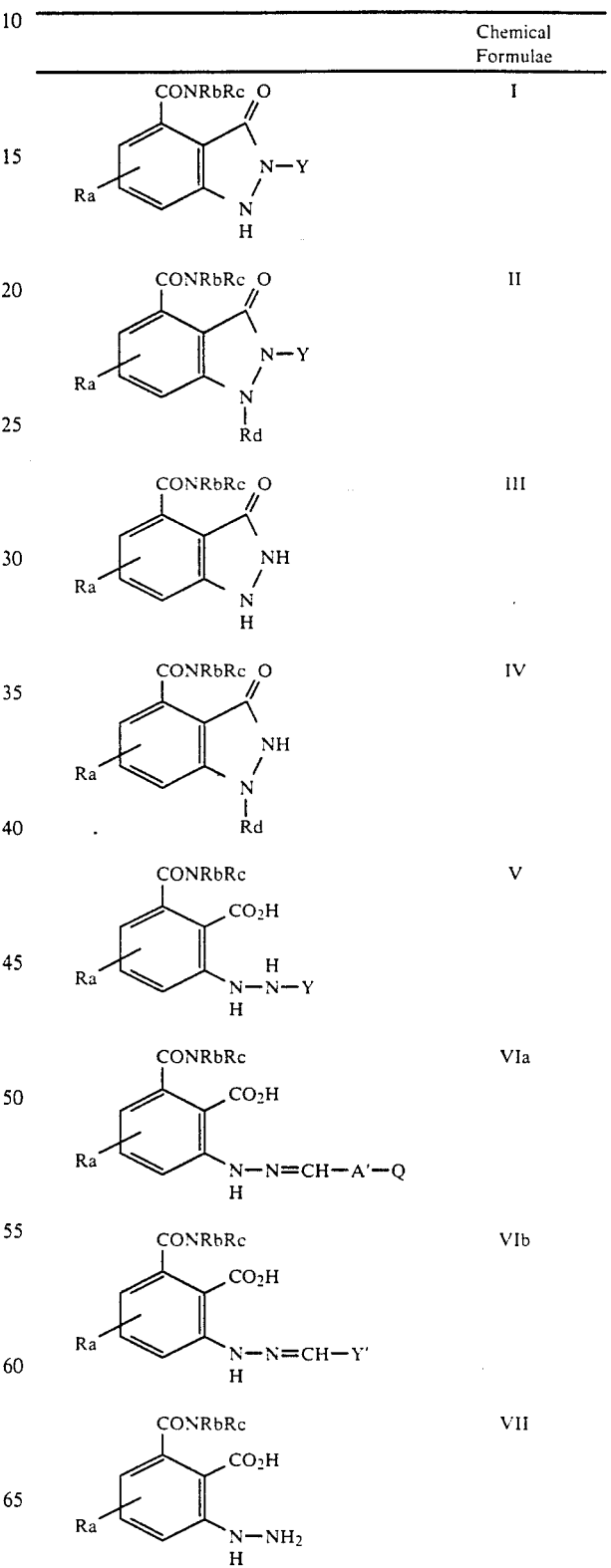

| Chemical Formulae |
|---|
| 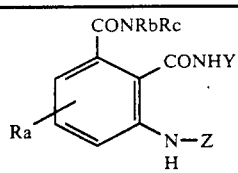 VIII |
| 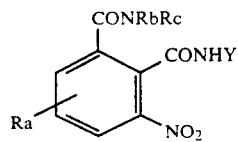 IX |
| 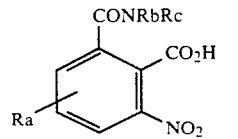 X |

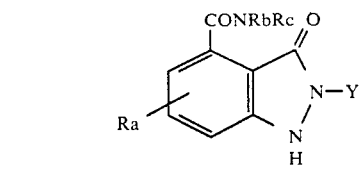  I

What we claim is:
1. A 1,2-dihydro-3H-indazol-3-one derivative of the formula I

| Chemical Formulae |
|---|
| 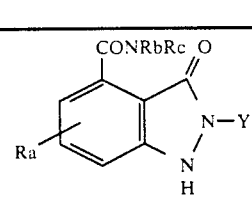 I |
| 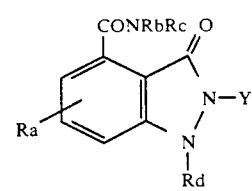 II |
| 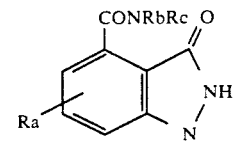 III |
| 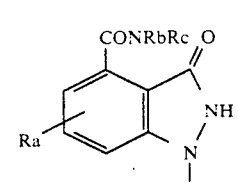 IV |

| Chemical Formulae |
|---|
| 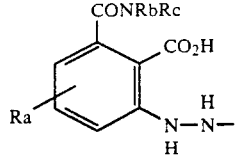 V |
| 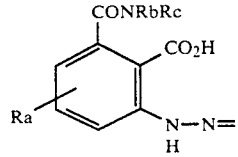 VIa |
| 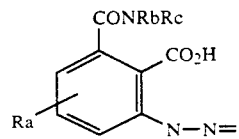 VIb |
| 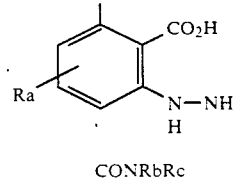 VII |
| 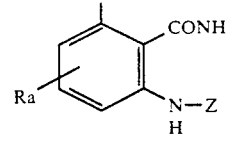 VIII |
| 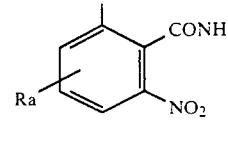 IX |
| 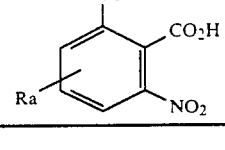 X |

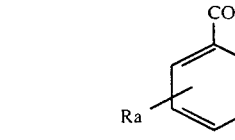 I

Ra is hydrogen, haogeno, hydroxy, cyano, Trifluoromethyl, (1-6C)alkyl or (1-6C)aloxy;
Rb is hydrogen or (1-6C) alkyl;
Rc is hydrogen, (1-8C)alkyl or (3-8C)alkenyl; and
Y is a group of the formula A-Q in which A is (1-6C-)alkylene or (3-6C)alkeneylene, and Q is pyridyl, which may optionally ear one or two substitutents selected from halogeno, hydroxy, cyano, trifuloromethyl, amino, nitro, (1-6C)alkyl, (1-6C)alkoxy, (1–6C)alkylamino, di[(1–4C)alkyl]amino or (2–6C-)alkanoylamino, or a pharmaceutically-acceptable salt thereof;

or a 1-(1–4C)alkoxycarbonyl derivative thereof.

2. An indazolone of the formula I as claimed in claim 1 wherein

Ra is hydrogen, fluoro, cholor, bromo, methyl, ethyl or methoxy;

Rb is hydrogen, methyl or ethyl;

Rc is hydrogen, methyl, ethyl, propyl, isopropyl, butyl, isobutyl, pentyl, hexyl, akkyl or methylallyl; and Y is a group of the formula —A-Q wherein A is methylene, ethylene, ethylidene, trimethylene, ethylidene or 2-propenylene, and Q is 3-pyridyl or 4-pyridyl which may be optionally bear a substituent selected from fluoro, chloro, bromo, amino, methyl, ethyl or methoxy;

or a pharmaceutically-acceptable salt thereof;

or a 1-(1–4C)alkoxycarbonyl derivative thereof.

3. An indazolone of the formula I as claimed in claim 1 wherein Ra is hydrogen; Rb is hydrogen; Rc is methyl, ethyl, propyl, butyl or pentyl; and Y is a group of the formula —A-Q wherein A is methylene and Q is 3-pyridyl;

or a pharmacetuical-acceptable salt thereof;

or a 1-(1–4C)alkoxycarbonyl derivative thereof.

4. A compound selected from the group consisting of 4-(N-methylcarbamoyl)-2-(3-pyridylmethyl)-, 4-(N-ethylcarbamoyl)-2-(3-pyridylmethyl)- and 4-(N-n-pentylcarbamoyl)-2-(3-pyridylmethyl)-1,2-dihydro-3H-indazol-3-one; or a pharmaceutically-acceptable salt thereof; or a 1-(1–4C)alkoxycarbonyl derivative thereof.

5. A pharamceutical composition which comprises an indazolone of the formula I as claimed in any one of claims 1 to 3, or a pharmaceutically-acceptable salt thereof, or a 1-(1–4C)alkoxycarbonyl derivative thereof, in association with a pharmaceutically-acceptable diluent or carrier.

6. An indazolone of the formula I as claimed in any one of claim 1 to 3 or a pharmaceutically-acceptable salt thereof, or a 1-(1–4C)alkoxycarbonyl derivative thereof, for use in medicine.

7. A method of treating a disease or medical condition mediated alone or in part by one or more leukotrienes which comprises administering to a warm-blooded animal requiring such treatment an effective amount of an indazolone of the formula I as claimed in any one of claims 1 to 3, or a pharmaceutically-acceptable salt thereof, or 1-(1–4C)alkoxycarbonyl derivative thereof.

* * * * *